United States Patent
Jones (12)

(10) Patent No.: US 6,718,267 B1
(45) Date of Patent: Apr. 6, 2004

(54) MONITORING THE CORROSION OF PIPELINES BY EVALUTING THE NOISE IN DATA SIGNALS TRANSMITTED VIA THE PIPELINE

(76) Inventor: Greg Jones, c/o Kairua Limited, 7a Ferryhill Place, Aberdeen AB11 2SE (GB)

(*) Notice: Subject to any disclaimer, the term of this patent is extended or adjusted under 35 U.S.C. 154(b) by 0 days.

(21) Appl. No.: 09/762,496
(22) PCT Filed: Aug. 9, 1999
(86) PCT No.: PCT/GB99/02621
§ 371 (c)(1), (2), (4) Date: Feb. 23, 2001
(87) PCT Pub. No.: WO00/08438
PCT Pub. Date: Feb. 17, 2000

(30) Foreign Application Priority Data

Aug. 8, 1998 (GB) .............................................. 9817221

(51) Int. Cl.[7] .............................. G01B 5/28; G01N 27/26
(52) U.S. Cl. .............................. 702/38; 702/33; 702/35; 204/404
(58) Field of Search ....................... 204/404; 205/775.5; 702/33–35, 36–38, 45, 47, 50–54; 324/207.12, 207.24, 72; 73/86, 570, 597, 627

(56) References Cited

U.S. PATENT DOCUMENTS

| | | | |
|---|---|---|---|
| 4,575,678 A | * 3/1986 | Hladky | ........................ 204/404 |
| 4,658,365 A | 4/1987 | Syrett et al. | |
| 4,886,360 A | 12/1989 | Finlan | |
| 5,139,627 A | * 8/1992 | Eden et al. | ................. 204/404 |
| 5,370,776 A | 12/1994 | Chen | |
| 6,298,732 B1 | * 10/2001 | Burnett | ........................ 73/579 |

FOREIGN PATENT DOCUMENTS

| | | |
|---|---|---|
| GB | 1 341 426 A | 12/1973 |
| GB | WO 93 26115 | * 12/1993 |
| WO | WO 93 26115 A | 12/1993 |
| WO | WO 94 12862 A | 6/1994 |

OTHER PUBLICATIONS

Lynn et al., *Introductory Digital Signal Processing*, Wiley, ISBN 0 471 97631 8. , pp. 316, 317, and 333–337.

Tadeusz et al., *Signal and Noise Separation: Art and Science*, Geophysics, vol. 64, No. 5., pp. 1648–1656.

Lacey, *Assessment of Noise Characteristics of Different Corrosion Processes in a Pipeline*, CAPCIS Reference BPJLGY/R1, Jun., 1999., 18 Pages.

Dougherty, P.E. et al., "Use of electrochemical noise measurement in the evaluation of materials for steam generators," Proceedings of the 1994 1st International.

Dickie Neil, "Corrosion monitoring in remote or hostile locations," Anticorrosion Methods and Materials, Jan.–Feb. 1997 MCB University Press LTD, Bradford, England, vol. 44, No. 1, pp. 41–43.

* cited by examiner

*Primary Examiner*—Bryan Bui
(74) *Attorney, Agent, or Firm*—Shalom Wertsberger; Saltamar Innovations

(57) ABSTRACT

When a pipeline is used as a medium for data transmission using a VLP or ELF Electro-magnetic signal the presence of corrosion effects on the pipeline lead to noise signals appearing in the received data signal. The present invention relates to a method of separating out this noise signal and analyzing it to determine the corrosion status of the pipeline. Both the type and location of the corrosion effect can be determined in this way.

8 Claims, 2 Drawing Sheets ating corrosion of pipelines by evaluating the noise in data signals transmitted via the pipeline

MONITORING THE CORROSION OF PIPELINES BY EVALUTING THE NOISE IN DATA SIGNALS TRANSMITTED VIA THE PIPELINE

This invention relates to a method of detecting and monitoring corrosion on both onshore and offshore pipelines especially but not exclusively by utilising low frequency signal propagation communication systems.

BACKGROUND OF THE INVENTION

Pipelines used for the transport of oil both on and offshore are subject to corrosion effects both from the material being transported and from the external environment. In order to ensure that the mechanical integrity of the pipeline is not compromised there is a need to monitor any corrosion that takes place. In certain circumstances, visual inspection of the pipeline is possible. However internal inspection and inspection of offshore pipelines in this way is generally not practical.

It is known that corrosion effects in a metallic pipeline will have an effect on electrical signals that are transmitted along a section of pipeline. Various proposals have previously been made to make use of electrical effects to monitor and measure corrosion rates in metal structures. Examples of methods for monitoring and measuring corrosion in metal structures using electrical techniques are described in U.S. Pat. Nos. 4,575,678, 4,658,365, 5,139,627 and 5,370,776. In each of these there is either a dedicated electrical connection made to the structure using parts of the structure to form electrodes or special electrodes attached to the structure. Various techniques are used for applying and analyzing electrical signals to obtain some measure of corrosion effects.

All of these techniques however share the disadvantage and limitation that they rely on the addition of extra components and specific dedicated external circuitry to the pipeline or structure in order to apply and measure electrical signals. In certain circumstances, for example offshore, this may be difficult to achieve.

SUMMARY OF THE INVENTION

It is an object of the present invention to provide a means of analyzing the electrical effects caused by corrosion in metal structures without the addition of extra external connections and circuitry.

According to the present invention there is provided a method of corrosion monitoring of pipelines comprising separating out a noise signal from a reference signal transmitted on a pipeline and analyzing said noise signal to provide an indication of the presence of corrosion effects.

Preferably the reference signal comprises a data communications signal.

The reference signal may be a DC signal or a low frequency AC signal. Most preferably, the reference signal has a signal frequency of around 100 Hz.

Preferibly also, the noise signal is separated out into elements representative of specific corrosion effects on the pipeline.

More preferably, the separate noise elements are analysed by comparison to noise signals representative of a range of corrosion effects to identify the presence and extent of any of said corrosion effects.

Most preferably, the separate noise elements are additionally analysed to determine the positional source of each noise element and so identify the location on the pipeline of each corrosion effect.

This may, for example, be by transmitting signals in both directions and analyzing their interaction.

The corrosion effects being monitored may for example include general corrosion, localised corrosion, sacrificial anode cathodic protection, $CO_2$ corrosion and seawater corrosion.

BRIEF DESCRIPTION THE DRAWINGS

Embodiments of the present invention will now be described by way of example with reference to the accompanying drawings in which.

DETAILED DESCRIPTION OF THE PREFERRED EMBODIMENT (S)

Figure 1:
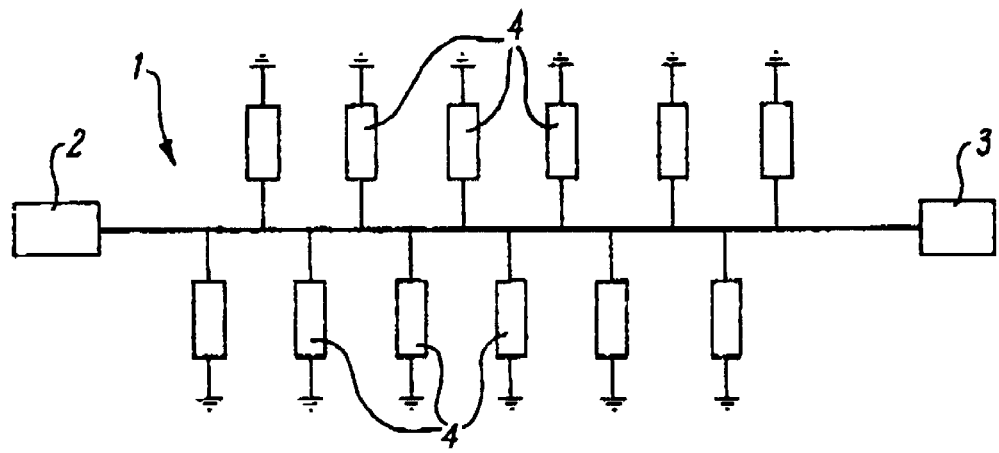
FIG. 1 is a schematic diagram illustrating the manner in which corrosion cells on a pipeline effectively create additional electrical inputs to a, signal being transmitted on said pipeline.

International Patent application number PCT/GB93/01272 describes a system for data transmission on pipelines. The system described is a low frequency communications system in which digital signals are transmitted along both onshore and offshore pipelines. Data is transmitted in either direction between a master platform and a remote, usually offshore, facility via communication channels formed by the electrically conducting material of the pipelines. The data is transmitted in the form of a VLF or ELF Electron-magnetic signal which comprises changes of voltage level oscillating about the DC voltage level of pipe so that the mean level of the signal is the DC voltage level of the pipe. The signal frequency is of the order of 100 Hz and as part of the data transmission system the received signal is analysed, using a series of signal processing algorithms, to remove noise picked up during transmission to produce a clean signal for data purposes. The presence of this noise is, at least partially, a result of corrosion effects on the surface, both internally and externally, of the pipeline. Thus while for data transmission purposes this noise is undesirable its very presence is on the other hand an indication of corrosion effects on the pipeline. While the above application recognises the cause of noise, its main concern is the removal of the noise effect from the data transmission.

Referring to the drawings the present invention is concerned with the analysis of the noise signal 10 that occurs in the transmitted signal 9 to provide a picture of the corrosion status 11 of the pipeline. The noise picked up on the transmitted signal is low frequency noise of typically <1 Hz. The noise has the spontaneous non-stoiochmetric electrochemical signal of low frequency (<1 Hz) and low amplitude (<10 mv) which is characteristic of the corrosion process and corrosion kinetics occurring on the metal surface. Thus by detailed analysis of the noise signal the presence of corrosion on the pipeline between the signal transmitter and receiver can be determined. Further developments may allow detailed analysis of the extent, type and location of the corrosion.

Figure 2:
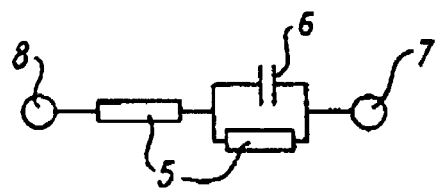
FIG. 2 is an effective circuit diagram of the corrosion cell that exists between the pipeline and seawater or ground.
Figure 3:
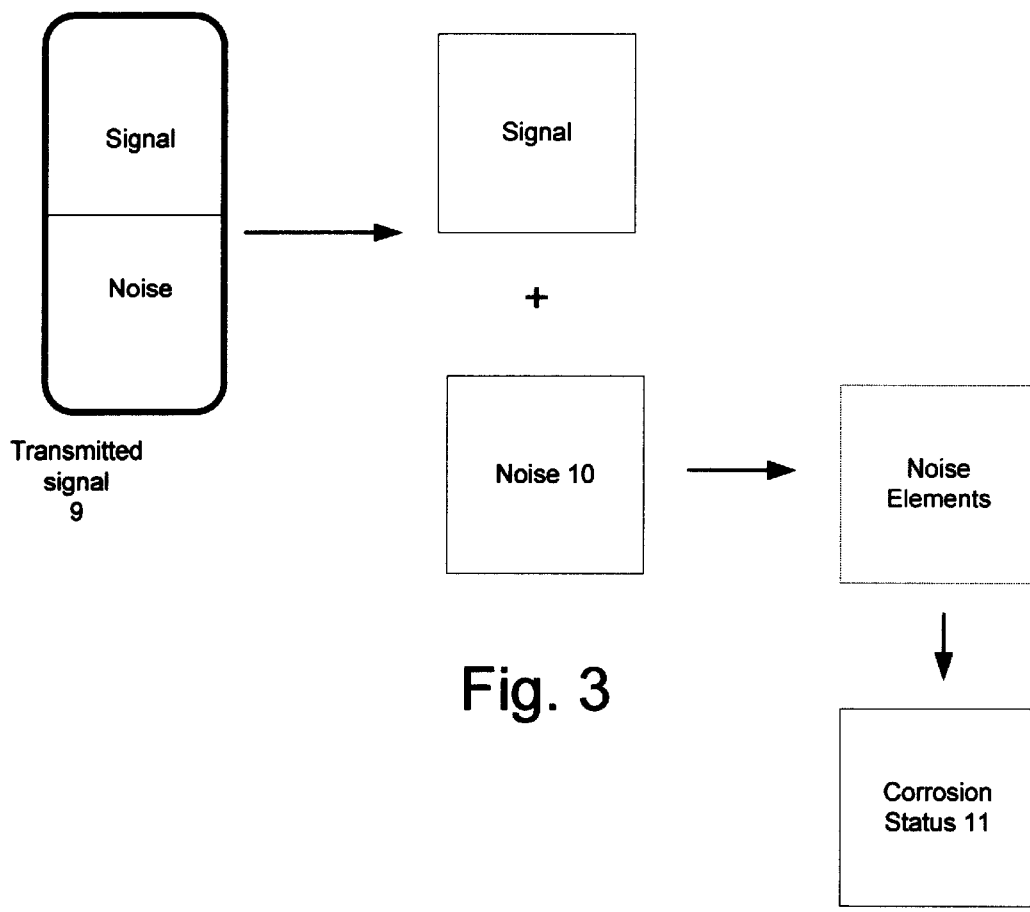
FIG. 3 is a schematic diagram illustrating separating out of a noise signal from a transmitted reference signal and further obtaining a corrosion status from the noise signal according to an embodiment of the present invention

More specifically the noise can be considered as the effect of the numerous parallel and series paths of corrosion cells associated with the pipeline. The electrochemical noise generated by these corrosion cells is effectively added to the data transmission signal. This can be seen in FIGS. 1 & 2 where a data transmission system is shown generally at 1 with a data transmitter 2 and a receiver 3 at respective ends of the system. A series of corrosion cells are represented by 4. The effective circuit of each corrosion cell 4 is shown generally in FIG. 2 being effectively a combination of resistive 5 and capacitive 6 elements between a pipeline 7 and ground 8.

Of course the noise signal is itself a composite signal representative of the cumulative effects of the various corrosion call paths. This noise signal will be made up of electrochemical noise associated with natural corrosion processes both generally and localised on joins and welds etc. both internally and externally and the effect of noise generated by sacrificial anodes.

By building up a database of the characteristics of the different electrochemical noises generated from different corrosion processes it is possible to have a means of identifying these corrosion processes when they occur in practice. Examples include general corrosion, localised corrosion, sacrificial anode cathodic protection, $CO_2$ corrosion, and seawater corrosion.

The present system analyses the noise signal to separate out and identify these individual noise elements in order that a picture can be created of the corrosion state of the section of pipeline. The analysis can be more or less complex depending on the level of detail required in the report to be created Modifications and improvements may be made without departing from the scope of the invention herein intended. For example although the embodiment described makes use of a data transmission system on the pipeline it is also envisaged that the system can be adapted for use on pipelines where no such data transmission system is in use. In such circumstances alternative arrangements can be provided for transmitting and receiving reference signals along the pipeline.

I claim:

1. A method of corrosion monitoring of pipelines comprising separating out a noise signal from a reference signal transmitted on a pipeline, separating out the noise signal into noise elements, and analyzing said noise elements by comparison to noise signals representative of a range of corrosion effects, to provide an indication of the presence of corrosion effects in the pipeline.

2. A method of corrosion monitoring of pipelines as claimed in claim 1, wherein the reference signal comprises a data communications signal.

3. A method of corrosion monitoring of pipelines as claimed in claim 1, wherein the reference signal has a signal frequency of around 100 Hz.

4. A method of corrosion monitoring of pipelines as claimed in claim 1, wherein the separate noise elements are analysed to determine the positional source of each noise element to identify the location on the pipeline of each corrosion effect.

5. A method of corrosion monitoring of pipelines as claimed in claim 4, wherein the signals are transmitted in both directions and interaction analysed to determine the positional source of each noise element.

6. A method of corrosion monitoring of pipelines as claimed in claim 1, wherein the corrosion effects being monitored include general corrosion, localised corrosion, sacrificial anode cathodic protection, $CO_2$ and seawater corrosion.

7. A method of corrosion monitoring of pipelines as claimed in claim 1, wherein said step of analyzing is conducted on a noise signal having a frequency of less than 1 Hz.

8. A method of corrosion monitoring of pipelines as claimed in claim 1, wherein said step of analyzing is conducted on a noise signal having an amplitude of less than 10 mV.

* * * * *